United States Patent [19]

Ohtombe et al.

[11] Patent Number: 4,764,969

[45] Date of Patent: Aug. 16, 1988

[54] APPARATUS FOR INSPECTING THE SURFACE OF A MATERIAL

[75] Inventors: Ko Ohtombe, Kanagawa; Masamitu Nishikawa, Yokosuka, both of Japan

[73] Assignee: Kabushiki Kaisha Toshiba, Kanagawa, Japan

[21] Appl. No.: 7,092

[22] Filed: Jan. 27, 1987

[30] Foreign Application Priority Data

Jan. 28, 1986 [JP] Japan ................................. 61-14701

[51] Int. Cl.$^4$ .............................................. G06K 9/00
[52] U.S. Cl. ........................................ 382/8; 358/106; 358/107
[58] Field of Search ..................... 382/8; 358/106, 107

[56] References Cited

U.S. PATENT DOCUMENTS

| 4,589,140 | 5/1986 | Bishop et al. | 382/14 |
| 4,593,406 | 6/1986 | Stone | 382/8 |
| 4,692,943 | 9/1987 | Pietzsch et al. | 358/106 |

Primary Examiner—Leo H. Boudreau
Attorney, Agent, or Firm—Finnegan, Henderson, Farabow, Garrett and Dunner

[57] ABSTRACT

An apparatus for inspecting the surface of a material having a first inspection section for inspecting the wide surface condition of a material with an analysis, a second inspection section for inspecting specific position's conditions of the surface of the material with finer analysis than that of the first inspection section, and a controller for controlling an inspecting position of the second inspection section to inspect an unusual position after the first inspection section finds the unusual position.

9 Claims, 4 Drawing Sheets

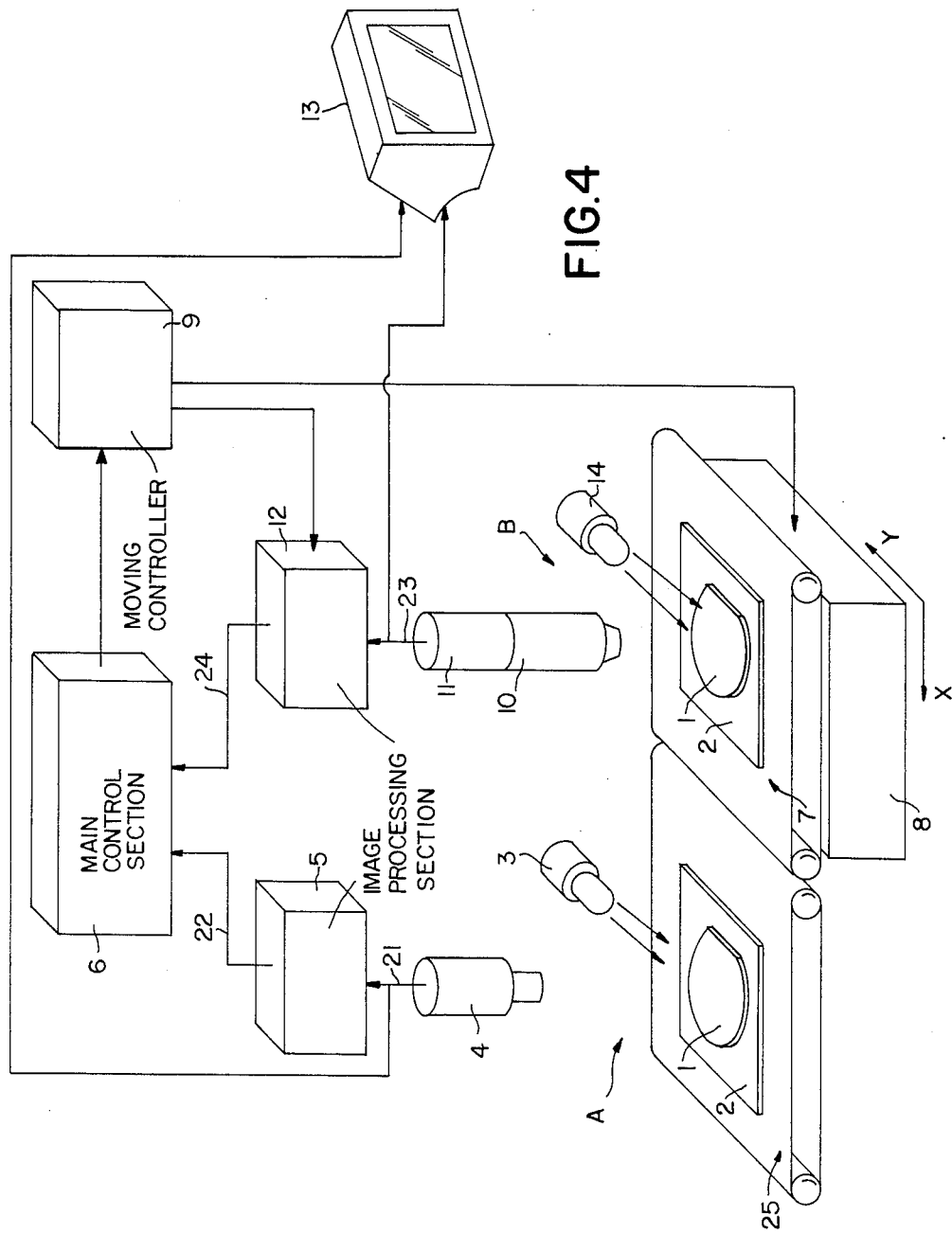

APPARATUS FOR INSPECTING THE SURFACE OF A MATERIAL

BACKGROUND OF THE INVENTION

1. Field of the Invention

This invention relates to an apparatus for inspecting semiconductor wafers.

2. Description of the Prior Art

In the process of producing integrated circuits, it is important to inspect wafers for improvement of the yield of the production. In particular, such inspection is extremely important in the photolithographic developing process, which coats photoresist on a wafer and forms a masked pattern on the wafer.

In the past, wafers have been manually inspected by special inspectors with their own eyes to judge the effectiveness of the production process. This inspection was broken down into whole wafer inspection using oblique light irradiation, i.e., macroscopic inspection, and inspection of certain points on a wafer surface using a microscope, i.e., microscopic inspection.

More recently, an inspecting apparatus having a carrying section has become available. This equipment stores the coordinates of pre-determined inspection points and permits whole wafer visual inspection and microscopic visual points inspection using a microscope without the need for manual contact with the wafer.

Even with this recent apparatus, however, macroscopic whole inspection and microscopic point inspection must be performed manually by special inspectors with their eyes for judgment. This requires training of special inspectors. Further, variations of inspection result from such factors as the health or subjective views of different inspectors.

SUMMARY OF THE INVENTION

Accordingly, it is an object of the present invention is to provide an improved inspecting apparatus for semiconductor wafers. It is a further object of the present invention to provide an automatic apparatus which is capable of automatically performing both macroscopic whole inspection and microscopic point inspection without the need for human visual inspection. Another object of the invention is to detect fine surface defects and improve inspection accuracy.

In accordance with the present invention, the foregoing objects are achieved by providing an apparatus for detecting defects in the surface of a material having macro inspection means for automatically producing a macro image of at least a portion of the surface of the material at a first resolution and for automatically detecting information on the location of surface defects on the portion, and control means connected to the macro inspection means for storing the location information detected by the macro inspection means.

Preferably, the apparatus also includes micro inspection means responsive to the control means for automatically producing a micro-image of a part of the overall surface of the material at a second resolution higher than the first resolution. The micro inspection means may be mounted in close proximity to the macro inspection means, and the apparatus also may include transport means for moving the material between a first position exposed to the macro inspection means and a second position exposed to the micro inspection means.

It is also preferred that the macro inspection means and the micro inspection means each include image formation means for producing the images of the material surface. The micro inspection means also may include microscope means for magnifying the image of the material surface received by the corresponding image formation means at the second resolution.

Preferably, image display means are provided for displaying images received from the respective image formation means. Movement means responsive to the control means may be included for positioning of the material with respect to the microscopic means.

It is preferred that the apparatus also includes image control means for comparing the brightness level of pre-determined portions of the macro image with a threshold brightness value.

BRIEF DESCRIPTION OF THE DRAWINGS

These and other objects and advantages of this invention will become more apparent and more readily appreciated from the following detailed description of the presently preferred exemplary accompanying drawings, of which:

FIG. 4 is a schematic illustration showing an automatic surface inspection apparatus according to another embodiment of the present invention.

DETAILED DESCRIPTION OF PREFERRED EMBODIMENT

One of the preferred embodiments of the present invention will be described with reference to the accompanying drawings.

Figure 1:
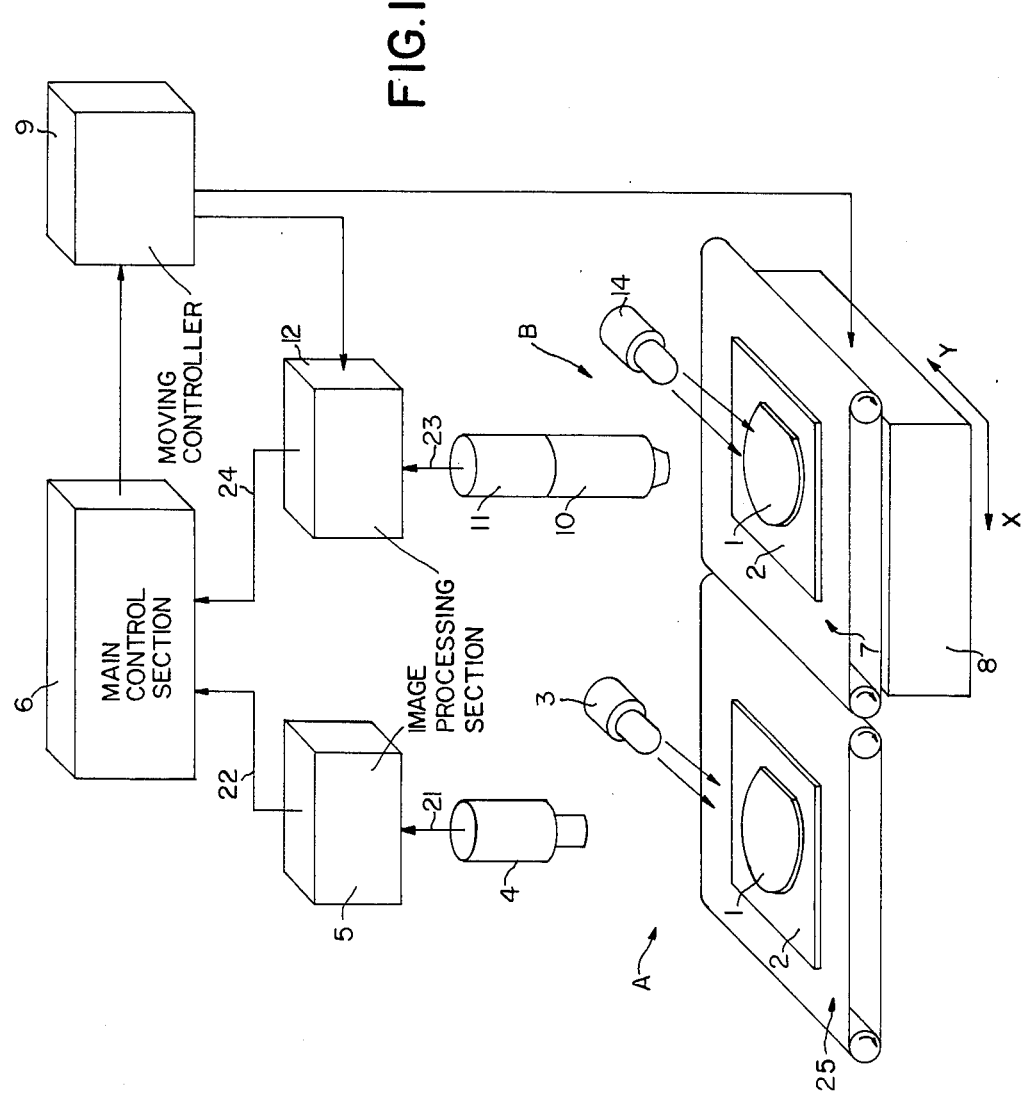
FIG. 1 is a schematic illustration showing an automatic surface inspection apparatus according to the present invention.

FIG. 1 shows an automatic surface inspection apparatus of the present invention by a schematic illustration. This apparatus may be used to inspect the surface of various materials, such as semiconductor wafers, original documents, masked pattern films, printed goods, pressed goods, etc.

Figure 2:
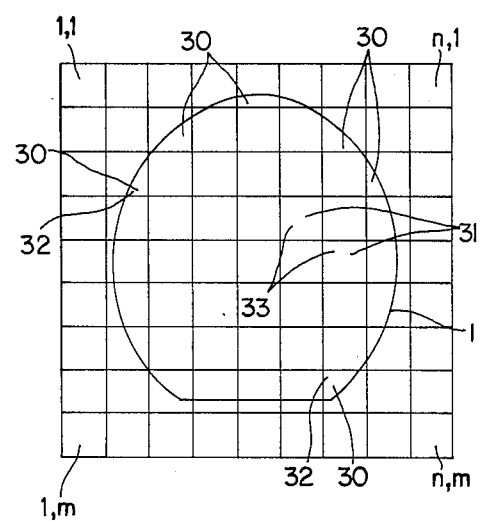
FIG. 2 is a plan view of a wafer image.

As shown in FIG. 1, this apparatus mainly comprises two sections (means), i.e., a macroscopic inspecting section A and a microscopic inspecting section B. The macroscopic inspecting section A is used, for example, to inspect a whole wafer surface, and the microscopic inspecting section B is used to inspect the particular points of the wafer surface in detail using a microscopic. In macroscopic inspecting section A, a wafer 1 to be inspected is mounted on a support 2, and the wafer surface is irradiated almost horizontally by light produced by a light source 3. The wafer 1 may be a pattern masked semiconductor wafer or non-masked wafer. Above the wafer 1, an industrial TV camera 4 (hereinafter called ITV camera) is installed. ITV camera 4 receives the wafer surface images which reflect from wafer 1. Images of the water surface by reflection are fed from the ITV camera 4 to an image processing section 5 through line 21. This image processing section 5 processes and analyses images entered from ITV camera 4 using a preset procedure with a difference of diffuse reflection and miller surface reflection. By these processes and analyses, image processing section 5 detects unusual (defective) positions on a wafer surface. Information on defects and defective positions is fed from image processing section 5 to a main control section 6 through line 22. As shown in FIG. 2, the surface image of wafer 1 is sectioned like a mesh to fit masked pattern(1,1-n,m), and these sectioned coordinates are used to inform main control section 6 of the coordinates of detected defective and potentially defective portions.

After the whole inspection at macroscopic inspecting section A is completed, wafer 1 is carried by carrying means 25 to microscopic inspecting section B. At microscopic inspecting section B, wafer 1 is mounted on a support 7. This support 7 is provided with moving member 8 that permits movement of the wafer in X and Y directions orthogonal to each other. This moving member 8 may be constructed according to various optional methods which are already known. A moving controller 9 controls moving member 8 for support 7. Moving controller 9 reads coordinate values stored in main control section 6, and drives moving member 8 so that wafer 1 may be positioned at a particular pre-determined point for inspection. Thus, the movement of support 7 can be controlled. Above wafer 1 positioned at the particular pre-determined point, a microscope 10 is installed, and the wafer surface is irradiated almost horizontally by light produced by a light source 14. An ITV camera 11 is installed above microscope 10, and receives microscopic images at the particular point on wafer 1 via microscope 10. The images are fed from the ITV camera 11 to an image processing section 12 through line 23. Image processing section 12 processes and analyses images entered from ITV camera 11 using the same sequence of image processing section 5. Then, the section 12 feeds information on the presence or absence of a defective portion to main control section 6 through line 24.

In the above description, image processing sections 5 and 12 are configured separately, but they may be configured integrally.

Figure 3:
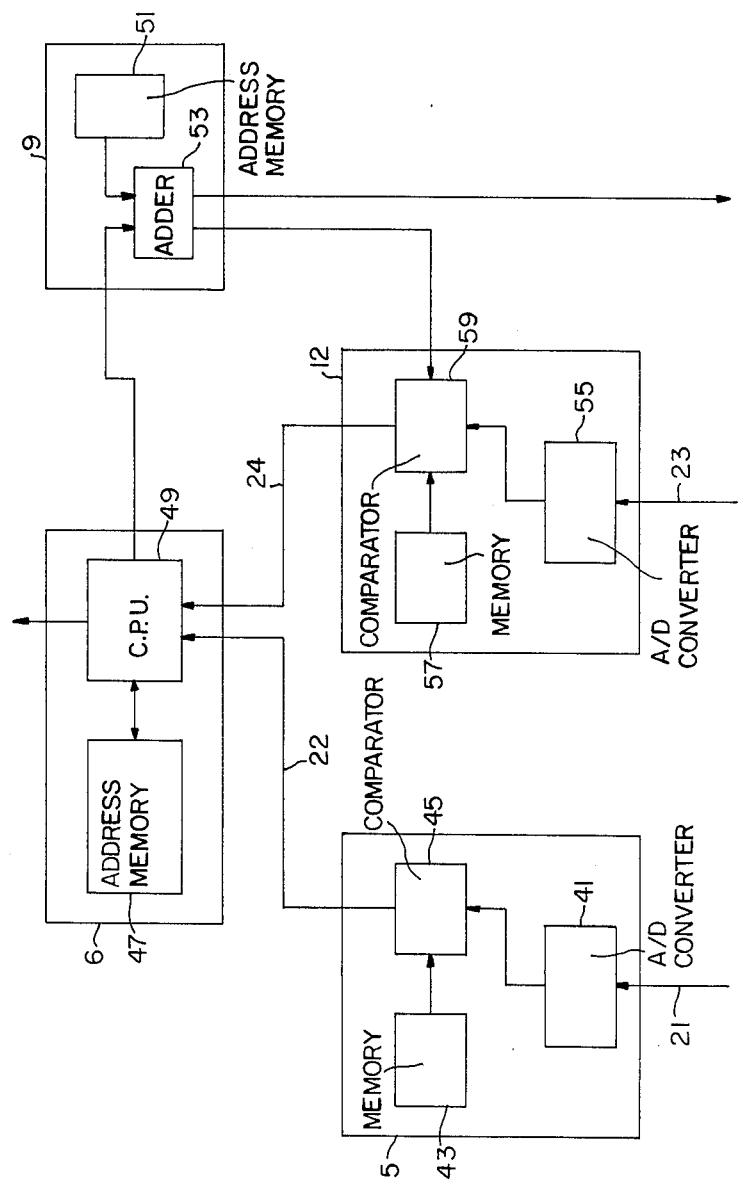
FIG. 3 is a partially schematic block diagram of the present invention.

FIG. 3 shows a partially block diagram of the present invention shown in FIG. 1. As shown FIG. 3, image processing section 5 comprises three sections (means), i.e., an analog/digital(A/D) conversion section 41, a memory section 43 and a comparison section 45. A/D conversion section 41 receives analog image data entered from ITV camera 4, and converts them to digital image data. Then A/D conversion section 41 sections those digital image data like a mesh to fit masked pattern(1,1-n,m) as shown in FIG. 2. Memory section 43 has information of threshold values in accordance with sectioned portions as shown in FIG. 2. Comparison section 45 compares the digital value generated by A/D conversion section 41 with the threshold value of memory section 43, and detects the defective and potentially defective portions. Information on the coordinate values corresponding to defective and potentially defective portions are transmitted to main control section 6 through line 22. Main control section 6 comprises two sections(means), an address memory section 47 and a central processing unit (CPU) section 49. Line 22 connects with CPU section 49. CPU section 49 receives the information on the coordinate values entered from image processing section 5 through line 22, and transmitts the information to address memory section 47. Then the information of the coordinate values from image processing section 5 is stored by address memory section 47. CPU section 49 also connects with line 24. Line 24 transmits information emitted by image processing section 12 to CPU section 49. Image processing section 12 comprises three sections(means), an A/D conversion section 55, a memory section 57, and a comparison section 59. A/D conversion section 55 receives analog image data entered from ITV camera 11 through line 23, and converts analog image data received from ITV camera 11 to digital values. Memory section 57 has information of threshold values. Comparison section 59 compares the values received from A/D conversion section 55 with the values memorized in memory section 57. Comparison section 59 transmits the result of the comparison to CPU section 49 of main control section 6 through line 24. Comparison section 59 continues to repeat the inspection when a control signal is times received from moving controller 9. Moving controller 9 comprises two sections(means), an address memory section 51 and an addition section 53. Address memory section 51 has information of particular pre-determined points for inspection, which micro inspection section B may always inspect. In addition, section 53 adds information from address memory section 51 and information from CPU section 49. CPU section 49 feeds information on the coordinate values corresponding to difective and potentially defective portions. Section 53 feeds information on inspection points to moving member 8 and information on inspection times to comparison section 59 in image processing section 12.

The above configuration of the present invention provides the following operation. In macroscopic inspecting section A, wafer 1 to be inspected is mounted on support 2, and light is applied almost horizontally onto the surface of wafer 1 from light surface 3. Reflection light from wafer 1 enters ITV camera 4, which shoots the surface images of wafer 1. These images are fed to A/D conversion section 41 in image processing section 5 through line 21. Image processing section 5 processes and analyses images entered from ITV camera 4 using a preset sequence to specify the presence or absence of defects and the defective portions. The difference of diffuse reflection and miller surface reflection is used for this processing and analysis, in accordance with well known techniques. If there is a scratch or a defect on the surface of the wafer 1, the scratch or the defect causes diffuse reflection. On the other hand the remaining portions of the surface cause miller reflection. Thus the images of unusual positions like scratches or defects appear brighter than those of the normal surface. This technique is disclosed in Japanese patent application No. 59-93187. As shown in FIG. 2, in A/D conversion section 41 of image processing section 5 the surface image of wafer 1 is sectioned like a mesh(1,1-n-m). Memory section 43 of image processing section 5 has information of the threshold value in accordance with the same coordinate values(1,1-n,m). Comparison section 45 compares digital image value of A/D conversion section 41 with the threshold value of memory section 43 per each image of sectioned areas(1,1-n,m). If the value of A/D conversion section 41 is higher than that of the threshold, the area is detected as a defective or potentially defective portion because there may be scratches or defects in the area. Information on the coordinate values corresponding to defective and potentially defective portions are transmitted to main control section 6 through line 22 and stored. For further detail, the information is transmitted from comparison section 45 in image processing section 5 to CPU section 49 in main control section 6 through line 22, and the information is stored in the address memory 47 by CPU section 49.

Wafer 1, which has been subjected to whole inspection in macroscopic inspecting section A, is carried by carrying means 25 to support 7 provided in microscopic inspecting section B. Moving controller 9 reads the coordinate values stored in address memory section 47 of main control section 6 for transmission to moving member 8 so that wafer 1 may be positioned at a particular pre-determined point. This makes it possible to control movement of support 7 in the X and Y directions to position wafer 1 at the particular pre-determined position. After wafer 1 has been positioned at this particular point, ITV camera 11 arranged above wafer 1 receives through microscope 10 images of the defective portions on the surface of wafer 1. These microscopic images produced by ITV camera 11 are transmitted to A/D conversion section 55 in image processing section 12 through line 23. These images should have a resolution of about 100 times that of macroscopic inspecting section a in order to distinguish clearly the defects and other unusual matters. For example, if the section A has a resolution of 100 $\mu$m, the section B should have a resolution of 1 $\mu$m or more. Image processing section 12 processes and analyses the microscopic image entered from ITV camera 11 using a method similar to that of image processing section 5, and it transmits information on the presence or absence of a defect to main control section 6. This section 12 determines whether the amount of the reflection or the area of the bright image is higher than a pre-determined criterion. This pre-determined criterion is memorized in memory section 57. A/D conversion section 55 converts the analog value entered from ITV camera 11 to digital value per each image. These digital values are compared with pre-determined criterion in memory section 57 by comparison section 59 per each image data of each mesh of the masked pattern area. Image processing section 12 continues the inspection procedure the times received from additional section 53 in moving controller 9. In this manner, it detects the presence of scratch shapes or wrinkle shapes in the mesh of the masked pattern area. As shown in FIG. 2, a scratch or a wrinkle 32 in the edge areas 30 of wafer 1 is considered safe, but those scratches or wrinkles 33 in the mask area 31 are treated as defects.

Moving controller 9 also stores the coordinate values of the pre-determined particular points. Moving controller 9 has address memory section 51 and additional section 53. Pre-determined particular points are memorized at address memory section 51. Then, if the macroscopic inspecting section A does not find an unusual or defective point, moving controller 9 moves support 7 by moving member 8, and microscopic inspecting section B checks the particular pre-determined points which are memorized at address memory section 51. If a defective or potentially defective portion has been detected on the surface of wafer 1 by macroscopic inspecting section A, main control section 6 stores the coordinate values on wafer 1 corresponding thereto at address memory section 47. After wafer 1 has been carried to microscopic inspecting section B and mounted on support 7, CPU section 49 in main control section 6 transmits to additional section 53 in moving controller 9 the coordinate values of the defective portion. Additional section 53 in moving controller 9 stores the coordinate values of the defective portion as well as those of the pre-determined particular points memorized at address memory section 51. Moving member 8 is driven by an output signal from additional section 53 in moving controller 9, permitting support 7 to be moved in the X and Y directions. Thus wafer 1 is positioned at not only defective portions, but also pre-determined points. Image processing section 12 continues to repeat the inspection procedure the times received from additional section 53. Hence, the defective and potentially defective portions can be inspected microscopically.

FIG. 4 shows another embodiment of the present invention. In FIG. 4, microscopic inspecting section B displays on a display monitor 13 the microscopic image produced by ITV camera 11 through microscope 10, and the image subjected to whole inspection by macroscopic inspecting section A. This embodiment permits the portions regarded as being potentially defective in macroscopic inspecting section A to be re-inspected in microscopic inspecting section B, and to be checked further by visual inspection by an inspector with display monitor 13. This may improve inspection accuracy and reliability further.

What is claimed is:

1. An apparatus for detecting defects in the surface of a material, comprising:
   macro inspection means for automatically producing a macro image of at least a portion of the surface of the material at a first resolution and for automatically detecting information identifying the location of the surface defects on the portion;
   control means connected to the macro inspection means for storing the location information detected by the macro inspection means; and
   micro insepction means responsive to said control means for automatically producing a micro-image of that part of the surface of the material identified by said macro inspection means as containing surface defect at a second resolution higher than the first resolution.

2. The apparatus of claim 1, wherein the micro inspection means is mounted in close proximity to the macro inspection means, and the apparatus includes transport means for moving the material between a first position exposed to the macro inspection means and a second position exposed to the micro inspection means.

3. The apparatus of claim 2, wherein the macro inspection means and the micro inspection means each include image formation means for producing the images of the material surface.

4. The apparatus of claim 3, also including image control means for comparing the brightness level of pre-determined portions of the macro-image with a threshold brightness value.

5. The apparatus of claim 3, wherein the micro inspection means also includes microscope means for magnifying the image of the material surface received by the corresponding image formation means at the second resolution.

6. The apparatus of claim 5, also including movement means responsive to the control means for positioning of the material with respect to the microscope means.

7. The apparatus of claim 5, also including image display means for displaying images received from the respective image formation means.

8. An apparatus for detecting defects in the surface of a material, comprising:
   macro inspection means for automatically producing a macro image of at least a portion of the surface of the material at a first resolution and for automatically detecting information identifying the location of surface defects on said portion;

micro inspection means for automatically producing a micro-image of at least certain predetermined portions of the surface of the material at a second resolution higher than said first resolution; and means for moving the micro inspection means to that portion of the surface of the material identified by the macro inspection means as containing surface defects to conduct a micro inspection of those portions in addition to said predetermined portions of said surface.

9. An apparatus for detecting defects in the surface of a semiconductor wafer, comprising:

macro inspection means for automatically producing a macro image of at least a portion of the surface of the semiconductor wafer at a first resolution and for automatically detecting information identifying the location of surface defects on the portion;

control means connected to the macro inspection means for storing the location information detected by the macro inspection means; and micro inspection means responsive to said control means for automatically producing a micro-image of the part of the surface of the semiconductor wafer identified by said macro inspection means as containing surface defect at a second resolution higher than the first resolution.

* * * * *